United States Patent
Epstein et al.

(10) Patent No.: US 7,220,582 B2
(45) Date of Patent: May 22, 2007

(54) STEM CELLS THAT TRANSFORM TO BEATING CARDIOMYOCYTES

(75) Inventors: Neal D. Epstein, Chevy Chase, MD (US); Thiru V. Gopal, North Potomac, MD (US); Steve O. Winitsky, Bethesda, MD (US); Shahin Hassanzadeh, Fairfax, VA (US)

(73) Assignee: United States of America as represented by the Secretary of the Department of Health and Human Services, Washington, DC (US)

( * ) Notice: Subject to any disclaimer, the term of this patent is extended or adjusted under 35 U.S.C. 154(b) by 193 days.

(21) Appl. No.: 10/863,004

(22) Filed: Jun. 7, 2004

(65) Prior Publication Data

US 2005/0058633 A1    Mar. 17, 2005

Related U.S. Application Data

(63) Continuation of application No. 10/003,400, filed on Oct. 22, 2001, now abandoned.

(51) Int. Cl.
    *C12N 5/02* (2006.01)
(52) U.S. Cl. .................... 435/325; 424/93.1; 424/93.2; 424/93.21; 435/325; 435/455
(58) Field of Classification Search ............... None
    See application file for complete search history.

(56) References Cited

U.S. PATENT DOCUMENTS

| 5,486,359 A | 1/1996 | Caplan et al. |
| 6,184,035 B1 * | 2/2001 | Csete et al. ............ 435/377 |
| 6,248,587 B1 | 6/2001 | Rodgers et al. |

FOREIGN PATENT DOCUMENTS

| WO | WO 99/03973 | 1/1999 |
| WO | WO 00/06701 | 2/2000 |
| WO | WO 01/00031 | 1/2001 |
| WO | WO 01/11011 | 2/2001 |

OTHER PUBLICATIONS

Pera et al, J Cell Science 2000 113: 5-10.*
Wobus et al, Physiol Rev 2005;85:635-78.*
Rust et al, In vitro Cell Dev Biol Anim 1997;33:270-6.*
Cornelison et al., "Single Cell Analysis of Regulatory Gene Expression in Quiescent and Activated Mouse Skeletal Muscle Satellite Cells," *Dev. Biol.* 191:270-283, 1997.
De Angelis et al., "Skeletal Myogenic Progenitors Originating from Embryonic Dorsal Aorta Coexpress Endothelial and Myogenic Markers and Contribute to Postnatal Muscle Growth and Regeneration," *J. Cell Biol.* 147:869-877, 1999.
Gopal et al., "A Novel Subpopulation of Adult Skeletal Muscle Cells Differentiates Into Beating Cardiomyocytes *in vitro*," *Mol. Biol. Cell* Nov. 12, 2001 (s):367a.
Gopal et al., "A Scal-Fraction of Cells from Murine Adult Skeletal Muscle Differentiates into Beating Cardiomyocytes *in vitro*," *Mol. Biol. Cell* Nov. 13, 2002 (s):418a.
Jackson et al., "Hematopoietic Potential of Stem Cells Isolated from Murine Skeletal Muscle," *Proc. Natl. Acad. Sci.* 96:14482-14486, 1999.
Jackson et al., "Regeneration of Ischemic Cardiac Muscle and Vascular Endothelium by Adult Stem Cells," *J.Clin. Invest.* 107:1395-1402, 2001.
Lee et al., "Clonal Isolation of Muscle-Derived Cells Capable of Enhancing Muscle Regeneration and Bone Healing," *J. Cell. Biol.* 150(5):1085-1100, 2000.
Makino et al., "Cardiomyocytes Can Be Generated from Marrow Stromal Cells *in vitro*," *J. Clin. Invest.* 103(5):697-705, 1999.
Orlic et al., "Bone Marrow Cells Regenerate Infarcted Myocardium," *Nature* 410:701-705, 2001.
Seale et al., "A new look at the origin, function, and 'stem-cell' status of muscle satellite cells," *Dev. Biol.* 218:115-124, 2000.
Yokoyama et al., "Muscle derived stem cells mediated ex-*vivo* gene transfer to the lower urinary tract; comparision of vectors," *J. Urol.* Supp. 163:39-40, 2000.
Qu et al., "Matching host muscle and donor myoblasts for myosin heavy chain improves myoblast transfer therapy," *Gene Therapy* 7:428-437, 2000.
Rando et al., "Primary Mouse Myoblast Purification, Characterization, and Transplantation for Cell-mediated Gene Therapy," *J. Cell Biol.* 125(6):1275-1287, 1994.
Watt et al., "Skeletal muscle stem cells: function and potential role in therapy," *Stem Cells*, Alphamed Press, Dayton, OH, p. 75-98, 1997.

* cited by examiner

*Primary Examiner*—Q. Janice Li
(74) *Attorney, Agent, or Firm*—Klarquist Sparkman, LLP

(57) ABSTRACT

Disclosed herein is a novel isolated population of stem cells, called spoc cells, that can be induced, either in vivo or in vitro, to differentiate into cardiomyocytes. Methods are disclosed herein to differentiate the spoc cells, and to utilize these spoc cells for screening agents that affect cardiomyocytes. Methods are also provided herein to utilize spoc cells in therapeutic applications for the treatment of myocardial defects, such as areas of ischemic or traumatic damage.

17 Claims, 2 Drawing Sheets

STEM CELLS THAT TRANSFORM TO BEATING CARDIOMYOCYTES

This is a continuation of U.S. patent application Ser. No. 10/003,400, filed Oct. 22, 2001, now abandoned, which is incorporated herein by reference.

FIELD

This application relates to the field of stem cells, specifically to methods of producing and differentiating muscle stem cells.

BACKGROUND

Many Americans die each year of congestive heart failure. Heart failure may occur from a variety of causes, including cardiomyopathy, myocardial ischemia, congenital heart disease, and valvular heart disease, resulting in cardiac cell death and myocardial dysfunction. As cardiomyocytes are not replaced in adult myocardial tissue, physiologic demands on the existing, healthy, cardiomyocytes leads to their hypertrophy. Heart transplants have been the only recourse for patients in end-stage heart disease, however the United Network of Organ Sharing (UNOS), has reported that although more than 40,000 patients were waiting for heart transplants as of February 2000, only 2,345 people received a donated heart in 1998. Furthermore, heart transplants are complicated by the incompatibility between the transplanted donor tissue and the recipient's immune system, which requires life-long immunosuppression. Yet another drawback of heart transplants is their high cost.

An alternative approach to heart transplantation is to generate cardiomyocytes from stem cells in vitro that can be used in the treatment of heart failure, and other cardiac diseases characterized by myocardial cell death or dysfunction. This approach is based on the ability of stem cells to both self-renew and differentiate into one or more mature cell types, including cardiomyocytes. Stem cells may be obtained from an individual suffering from heart disease and then used to generate cardiomyocytes in vitro in order to repair the damaged myocardium. This approach avoids problems inherent with heart transplantation, such as lack of a suitable heart for transplant or immune rejection of a transplanted heart.

Embryonic stem (ES) cells, derived from the inner cell mass of the blastocyst, are the most primitive stem cell, as disclosed in WO 01/11011 A2. These cells have unlimited self-renewal capability, and because they can differentiate into several cell lineages and repopulate tissues upon transplantation, they have multipotent differentiative potential. However, protocols are not available for differentiating embryonic stem cells into beating cardiomyocytes.

Lineage specific stem cells, identified in most organ tissues, have less self-renewal capability than ES cells and their differentiative ability is limited to tissues of that lineage. Of the lineage specific stem cells, the hematopoietic stem cell (HSC), derived from bone marrow, blood, cord blood, fetal liver and yolk sack, is the best characterized. These cells are defined by the expression of cell surface markers, such as c-kit (c-kit+), and can terminally differentiate into all the hematopoietic cell types. HSC have been shown to contribute to the formation of functional cardiac tissue in vivo (Jackson et al, J. Clin. Invest., 107:1395–1402, 2001). Mesenchymal stein cells (MSC) are pluripotent progenitor cells derived from tissues of mesodermal origin (U.S. Pat. No. 5,486,359). These cells are most often obtained from bone marrow, although they can be obtained from other sources, such as blood or dermis. These cells have been shown to differentiate to form muscle, bone, cartilage, fat, marrow stroma and tendon, but have not been shown to differentiate into cardiomyocytes. In addition, progenitor cells have been identified in skeletal muscle, termed satellite cells (Cornelison and Wold, Dev. Biol., 191:270–283, 1997). These cells are characterized by the expression of the cell surface marker c-met (c-met+) in both its quiescent and activated states. When activated these cells re-enter the cell cycle, express myogenic regulatory factors, and differentiate into myoblasts.

However, despite the existence of a variety of stem cells, there is currently no pure population of stem cells that can be induced under defined conditions to differentiate into spontaneously beating cardiomyocytes in vitro. Thus, there remains a need in the art for isolated populations of stem cells which can be induced to differentiate into cardiomyocytes.

SUMMARY

The methods and cells described herein are based on the ability of certain stem cells to be differentiated in vitro to form a fully functional cell of more than one given cell type.

Disclosed herein is a novel isolated population of stem cells, called spoc cells, that can be induced, either in vivo or in vitro, to differentiate into cardiomyocytes. Methods are disclosed herein to differentiate the spoc cells, and to utilize these spoc cells for screening agents that affect cardiomyocytes. Methods are also provided herein to utilize spoc cells in therapeutic applications.

The foregoing and other objects, features, and advantages will become more apparent from the following detailed description of a several embodiments which proceeds with reference to the accompanying figures.

BRIEF DESCRIPTION OF THE FIGURES

FIG. 1A is a digital image of CS cell at day 3 with disordered myosin filaments. FIG. 1B is a digital image showing that at day 7 myosin filaments of characteristic 1.6 μm-length (top box) radiate outward and the cells contain dense bodies (lower box). FIG. 1C and FIG. 1F are digital images of a cell at day 14, showing a single, central nucleus shows a stretching out of the dense bodies into an organizing sarcomere. FIG. 1D shows that day 3 CS cells are round cells with copious mitochondria (box and detail). FIG. 1E shows elongated day 7 cells contain dense bodies (arrowhead). FIG. 1G shows that by day 56, a well-defined sarcomere (FIG. 1G) is present, with identifiable A- and I-bands and Z-lines.

FIG. 2A shows a graphical representation of the calcium transient in a beating CS cell-derived cardiomyocyte. Peak intensity and baseline are shown in FIG. 2B and FIG. 2C, respectively.

DETAILED DESCRIPTION OF SEVERAL EMBODIMENTS

Figure 1:
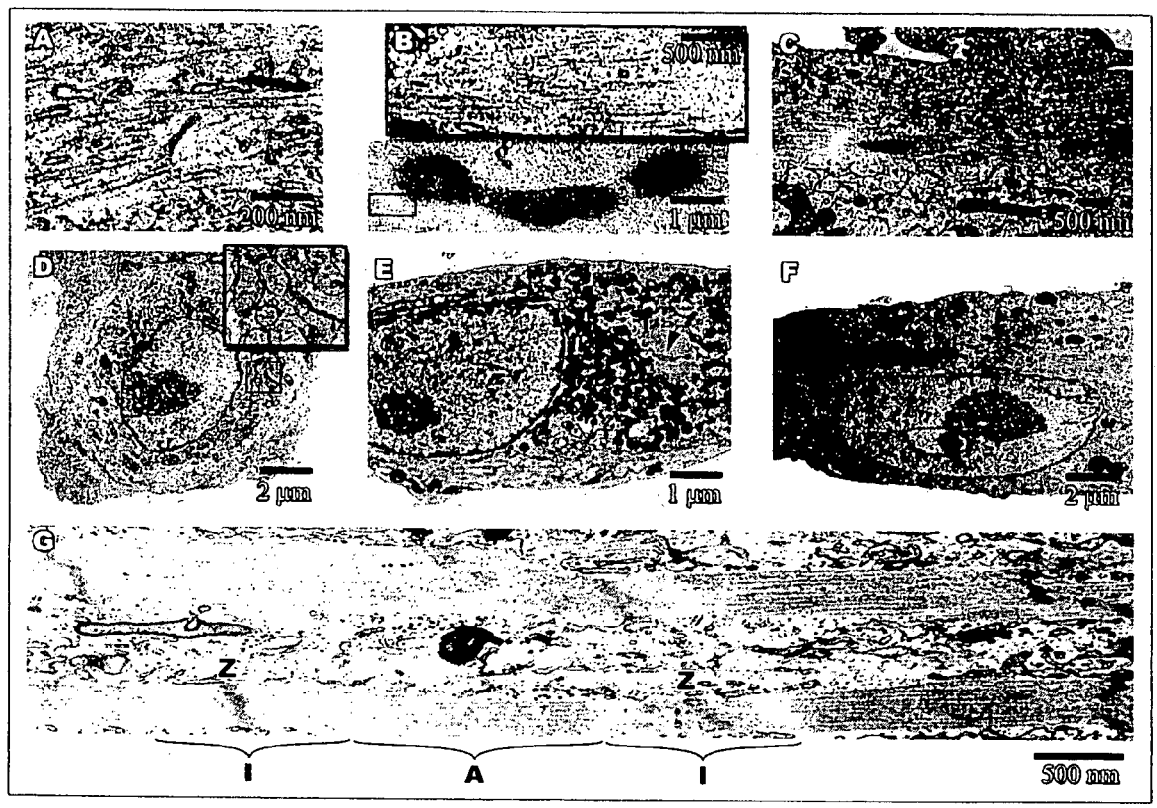
FIG. 1 is a series of digital images of transmission electron micrographs demonstrating the progression of differentiation of CS (cardiac precursor from spoc cells) cells over time when cultured in differentiation medium.

In order to facilitate review of the various embodiments disclosed herein, the following list of abbreviations and explanation of terms is provided:

I. Abbreviations and Terms
  A. Abbreviations
  CS: Cardiac precursors from spoc cells
  DNA: Deoxyribonucleic acid
  EGF: Epidermal growth factor
  EGFP: Enhanced green fluorescent protein
  ES: Embryonic stem
  FACS: Fluorescence activated cell sort
  FBS: Fetal bovine serum
  FGF: Fibroblast growth factor
  HSC: Hematopoietic stem cell
  MRNA: Messenger ribonucleic acid
  PBS: Phosphate buffered saline
  RNase: Ribonuclease
  RT-PCR: Reverse transcriptase-polymerase chain reaction
  SPOC: Skeletal-based precursors of cardiomyocytes
  B. Terms
  Unless otherwise noted, technical terms are used according to conventional usage. Definitions of common terms in molecular biology may be found in Benjamin Lewin, *Genes VI*, published by Oxford University Press, 1997 (ISBN 0-19-857778-8); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8)

Adult: A fully developed and physically mature subject, having attained full size and strength.

Animal: Living multi-cellular vertebrate organisms, a category that includes, for example, mammals and birds.

Cardiac: Pertaining to the heart.

Cardiac dysfunction: Any impairment in the heart's pumping function. This includes, for example, impairments in contractility, impairments in ability to relax (sometimes referred to as diastolic dysfunction), abnormal or improper functioning of the heart's valves, diseases of the heart muscle (sometimes referred to as cardiomyopathy), diseases such as angina and myocardial ischemia and infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart (for example, atrial septal defect). For further discussion, see Braunwald, Heart Disease: a Textbook of Cardiovascular Medicine, 5th edition 1997, WB Saunders Company, Philadelphia Pa. (hereinafter Braunwald).

Cardiac muscle: The heart is made of specialized muscle tissue with some similarities to both smooth and skeletal muscle. It is involuntary and mononucleate as is smooth muscle. Cardiac muscle is striated like skeletal muscle, which means that it has microscopically visible myofilaments arranged in parallel with the sarcomere. These filaments slide along each other during the process of contraction in the same manner as occurs in skeletal muscle. However, cardiac muscle contains more mitochondria so the striations are not as organized as they are in skeletal muscle. Cardiac muscle also differs from skeletal muscle in that the fibers in cardiac muscle branch and usually have a single centrally located nucleus. Another difference in cardiac muscle is the presence of intercalated discs which serve as specialized connections between cardiac muscle cells. These tight connections allow for almost completely free movement of ions so that action potentials can freely pass from one cell to another. This arrangement makes cardiac muscle tissue a functional syncytium. When one cell is excited the resultant action potential is spread to all of them. This is an important feature in that it allows the atrial or ventricular muscle to contract as a unit to forcefully pump blood. Cardiac muscle can generate its own excititory impulses from the sino-atrial node, which acts like a biological pacemaker. In this manner, the contracting signal for cardiac muscles originates in the heart itself. However, the autonomic nervous system (for example through the vagus nerve) can exert control over how fast the signals form and propagate through the heart, which regulates the rate of myocardial contraction. A "cardiomyocyte" is a cell of the cardiac muscle.

Cardiac precursors from spoc cells (CS cells): When spoc cells are isolated from skeletal muscle and are cultured under growth conditions designed to promote their growth, spoc cells undergo several rounds of division. During this proliferative phase they become clusters of floating round cells with an increased diameter as compared to spoc cells. These round cells, with an increased diameter, are referred to as CS cells. In one embodiment, a diameter of a CS cell is from about 10 to about 14 µm. When placed in growth promoting conditions in vitro (such as the examples described below) CS cells differentiate into spontaneously beating cardiomyocytes.

Cardiomyopathy: Any disease or dysfunction of the myocardium (heart muscle) in which the heart is abnormally enlarged, thickened and/or stiffened. As a result, the heart muscle's ability to pump blood is usually weakened. The disease or disorder can be, for example, inflammatory, metabolic, toxic, infiltrative, fibroplastic, hematological, genetic, or unknown in origin. There are two general types of cardiomyopathies: ischemic (resulting from a lack of oxygen) and nonischemic. Ischemic cardiomyopathy is a chronic disorder caused by coronary artery disease—a disease in which there is atherosclerotic narrowing or occlusion of the coronary arteries on the surface of the heart. Coronary artery disease often leads to episodes of cardiac ischemia, in which the heart muscle is not supplied with enough oxygen-rich blood. Eventually, the heart muscle enlarges from the additional work it must do in the absence of sufficient oxygen-rich blood.

Nonischemic cardiomyopathy is generally classified into three groups based primarily on clinical and pathological characteristics:
  (1) dilated cardiomyopathy, a syndrome characterized by cardiac enlargement and impaired systolic function of one or both ventricles;
  (2) hypertrophic cardiomyopathy, herein defined as (a) global or regional increase in thickness of either ventricular wall or the interventricular septum, or (b) an increased susceptibility to global or regional increase in thickness of either ventricular wall or the interventricular septum, such as can occur in genetic diseases, hypertension, or heart valve dysfunction; or
  (3) restrictive and infiltrative cardiomyopathies, a group of diseases in which the predominant clinical feature is usually impaired ability of the heart to relax (diastolic dysfunction), and is often characterized by infiltration of the heart muscle with foreign substances such as amyloid fibers, iron, or glycolipids.

See Wynne and Braunwald, The Cardiomyopathies and Myocarditities, Chapter 41, supra.

Cell surface marker: A protein, glycoprotein, or other molecule expressed on the surface of a cell, which serves to help identify the cell. A cell surface marker can generally be detected by conventional methods. Specific, non-limiting examples of methods for detection of a cell surface marker are immunohistochemistry, fluorescence activated cell sorting (FACS), or an enzymatic analysis.

Congenital heart disease: A heart-related problem that is present since birth and often as the heart is forming even before birth. Congenital heart disease may affect the heart, the heart's valves, the veins leading to, or the arteries leading away, from the heart, or the connections between these parts of the body.

Differentiation: The process whereby relatively unspecialized cells (e.g., stem cells) acquire specialized structural and/or functional features characteristic of mature cells. Similarly, "differentiate" refers to this process. Typically, during differentiation, cellular structure alters and tissue-specific proteins appear. The term "differentiated muscle cell" refers to cells expressing a protein characteristic of the specific muscle cell type. A differentiated muscle cell includes a skeletal muscle cell, a smooth muscle cell, and a cardiac muscle cell.

Differentiation Medium A synthetic set of culture conditions with the nutrients necessary to support the growth or survival of cultured cells, and which allows the differentiation of stem cells into differentiated cells.

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The tern codon is also used for the corresponding (and complementary) sequences of three nucleotides in the mRNA into which the DNA sequence is transcribed.

Epidermal growth factor (EGF): In particular examples, EGF is a globular protein of 6.4 kDa consisting of 53 amino acids. It contains three intramolecular disulfide bonds essential for biological activity. EGF proteins are evolutionarily closely conserved. Human EGF and murine EGF have 37 amino acids in common. Approximately 70 percent homology is found between human EGF and EGF isolated from other species. Mammalian EGF includes, but is not limited to, murine, avian, canine, bovine, porcine, equine, and human EGF. The amino acid sequences and methods for making these EGF polypeptides are well known in the art.

The gene encoding the EGF precursor has a length of approximately 110 kb, and contains 24 exons. Fifteen of these exons encode protein domains that are homologous to domains found in other proteins. The human EGF gene maps to chromosome 4q25-q27.

EGF is a strong mitogen for many cells of ectodermal, mesodermal, and endodermal origin. EGF controls and stimulates the proliferation of epidermal and epithelial cells, including fibroblasts, kidney epithelial cells, human glial cells, ovary granulosa cells, and thyroid cells in vitro. EGF also stimulates the proliferation of embryonic cells. However, the proliferation of some cell lines has been shown to be inhibited by EGF.

EGF is also known to act as a differentiation factor for some cell types. It strongly influences the synthesis and turn-over of proteins of the extra-cellular matrix including fibronectin, collagen, laminin, and glycosaminoglycans, and has been shown to be a strong chemoattractant for fibroblasts and epithelial cells.

EGF can be assayed in a cell-based assay wherein the proliferation of a cell population is assessed. EGF can also be assayed by an immunoassay, such as an ELISA assay.

Fragments of EGF, smaller than the full-length sequence can also be employed in methods disclosed herein. Suitable biologically active variants can also be utilized. One specific, non-limiting example of an EGF variant of use is an EGF sequence having one or more amino acid substitutions, insertions, or deletions, wherein a biological function of EGF is retained. Another specific, non-limiting example of an EGF variant is EGF as wherein glycosylation or phosphorylation is altered, or a foreign moiety is added, so long as a biological function of EGF is retained. Methods for making EGF fragments, analogues, and derivatives are available in the art. Examples of EGF variants are known in the art, for example U.S. Pat. No. 5,218,093 and WO 92/16626A1. Examples of EGF from many different species are disclosed in WO 92/16626A1, as are examples of variants, and strategies for producing them.

As used herein, "EGF" refers to naturally occurring EGF, and variants and fragments that perform the same function of EGF in the culture media disclosed herein.

Embryonic stem (ES) cells are totipotent cells isolated from the inner cell mass of the developing blastocyst and can generate all of the cells present in the body (bone, muscle, brain cells, etc.). "ES cells" can be derived from any organism, for example from mammals such as humans.

Fibroblast growth factor (FGF): Any suitable fibroblast growth factor, derived from any animal, and functional variants and fragments thereof. A variety of FGFs are known and include, but are not limited to, FGF-1 (acidic fibroblast growth factor), FGF-2 (basic fibroblast growth factor, bFGF), FGF-3 (int-2), FGF-4 (hst/K-FGF), FGF-5, FGF-6, FGF-7, FGF-8, and FGF-9. FGF refers to a fibroblast growth factor protein such as FGF-1, FGF-2, FGF-4, FGF-6, FGF-8, or FGF-9, or a biologically active fragment or mutant thereof. The FGF can be from any animal species. In one embodiment the FGF is mammalian FGF including but not limited to, rodent, avian, canine, bovine, porcine, equine, and human. The amino acid sequences and method for making many of the FGFs are well known in the art.

Fragments of FGF that are smaller than those described can also be employed.

Suitable biologically active variants can be FGF analogues or derivatives. An analogue of FGF is either FGF or an FGF fragment that includes a native FGF sequence and structure having one or more amino acid substitutions, insertions, or deletions. Analogs having one or more peptoid sequences (peptide mimic sequences) are also included (see e.g. International Publication No. WO 91/04282). By "derivative" is intended any suitable modification of FGF, FGF fragments, or their respective analogues, such as glycosylation, phosphorylation, or other addition of foreign moieties, so long as the FGF activity is retained. Methods for making FGF fragments, analogues, and derivatives are available in the art.

Growth factor: A substance that promotes cell growth, survival, and/or differentiation. In general, growth factors stimulate cell proliferation or maturation when they bind to their receptor. In one embodiment, growth factors are a complex family of polypeptide hormones or biological factors that control growth, division, and maturation of muscle cells. In another embodiment a growth factor can be used to promote the proliferation of muscle stem cells and maintain the stem cells in an undifferentiated state. A growth factor can be a naturally occurring factor or a factor synthesized using molecular biology techniques. Examples of growth factors include platelet-derived growth factor, fibroblast growth factor, epidermal growth factor, insulin, somatomedin, stem cell factor, vascular endothelial growth factor, granulocyte colony stimulating factor, and transforming growth factor-beta, amongst others. A muscle cell growth factor is a growth factor that effects the development (maturation), differentiation, division, or proliferation of muscle cells.

Growth medium: A synthetic set of culture conditions with the nutrients necessary to support the growth or survival of microorganisms or culture cells.

Heart: The muscular organ of an animal that circulates blood. The walls of the heart are comprised of working muscle, or myocardium, and connective tissue. Myocardium is comprised of myocardial cells, which are also referred to herein as cardiac cells, cardiac myocytes, cardiomyocytes and/or cardiac fibers. Cardiomyocytes may be cells of the atrium or cells of the ventricle.

Heart failure: The inability of the heart to supply sufficient oxygenated blood to meet the metabolic needs of the tissues and cells in a subject. This can be accompanied by circulatory congestion, such as congestion in the pulmonary or systemic veins. As used herein, the term heart failure encompasses heart failure from any cause, and is intended herein to encompass terms such as "congestive heart failure," "forward heart failure," "backward heart failure," "high output heart failure," "low output heart failure," and the like. See Chapters 13–17 in Braunwald for a detailed discussion. Conditions that could lead to heart failure include, but are not limited to, coronary artery disease, cardiomyopathy, or congenital heart disease.

Heterologous: A heterologous sequence is a sequence that is not normally (i.e. in the wild-type sequence) found adjacent to a second sequence. In one embodiment, the sequence is from a different genetic source, such as a virus or organism, than the second sequence.

Isolated: An "isolated" biological component (such as a nucleic acid molecule, protein or organelle) has been substantially separated or purified away from other biological components in the cell of the organism in which the component naturally occurs, i.e., other chromosomal and extrachromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Mammal: This term includes both human and non-human mammals. Similarly, the term "subject" includes both human and veterinary subjects.

Muscle cell: Includes skeletal, cardiac or smooth muscle tissue cells. This term is synonymous with myocyte, and encompasses those cells which differentiate to form more specialized muscle cells (e.g. myoblasts). "Cardiomyocyte" refers to a cardiac muscle cell.

Myocardial injury: Damage to the muscle or the "myocardium" in the wall of the heart as a result of disease or trauma. Myocardial injury can be attributed to many things such as, but not limited to, cardiomyopathy, myocardial infarction, or congenital heart disease.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Pharmaceutically acceptable carriers: *Remington'S Pharmaceutical Sciences*, by E. W. Martin, Mack Publishing Co., Easton, Pa., 15th Edition (1975), describes compositions and formulations suitable for pharmaceutical delivery of stem cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: Refers to a chemical compound or composition capable of inducing a desired therapeutic or prophylactic effect when properly administered to a subject or a cell. "Incubating" includes exposing a target to an agent for a sufficient period of time for the agent to interact with a cell. "Contacting" includes incubating an agent in solid or in liquid form with a cell.

Polypeptide refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those which are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence. Programs and algorithms for determining percentage identity can be found at the NCBI website.

Precursor Cell: A cell that can generate a fully differentiated functional cell of at least one given cell type. Generally, precursor cells can divide. After division, a precursor cell can remain a precursor cell, or may proceed to terminal differentiation. A "muscle precursor cell" is a precursor cell that can generate a fully differentiated functional muscle cell, such as a cardiomyocyte or a skeletal muscle cell. One specific, non-limiting example of a muscle precursor cell is a "cardiac precursor cell," which is a cell that gives rise to cardiac muscle cells.

Progenitor Cell: A cell that gives rise to progeny in a defined cell lineage. A "muscle progenitor cell" is a cell that gives rise to cells of the muscle lineage. One specific, non-limiting, example of a skeletal muscle progenitor cell is a "satellite cell," which gives rise to immature and mature skeletal muscle cells.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Similarly, a recombinant protein is one encoded for by a recombinant nucleic acid molecule.

Skeletal muscle: Skeletal muscle makes up most of the body's muscle and does not contract without nervous stimulation. It is under voluntary control and lacks anatomic cellular connections between fibers. The fibers (cells) are multinucleate and appear striated due to the arrangement of actin and myosin protein filaments. Each fiber is a single cell, long, cylindric and surrounded by a cell membrane. The muscle fibers contain many myofibrils that are made of myofilaments. These myofilaments are made up of contractile proteins. The key proteins in muscle contraction are myosin, actin, tropomyosin and troponin.

Skeletal-based precursor of cardiomyocytes (Spoc) cells: Stem cells derived from skeletal muscle, which do not express the cell surface markers c-met, or c-kit, that can be differentiated into cardiomyocytes. In one embodiment spoc cells are muscle derived precursor cells that are about 4 μm in diameter when cultured in vitro. These cells remain in suspension and proliferate when cultured in the presence of a growth factor. Specific, non-limiting examples of growth factors of use in propagating spoc cell are FGF, EGF, or a combination thereof.

In one embodiment, spoc cells differentiate into spontaneously beating cardiomyocytes in vitro. During a proliferative phase (e.g. about 7 days after being maintained in vitro in the presence of a growth factor), spoc cells cluster and increase in size to about 10–14 μm in diameter. The cells in these clusters, referred to as CS cells, have the ability to differentiate into mature cardiac muscle cells when cultured in the absence of growth factors. Methods for isolating and differentiating spoc cells are disclosed herein.

Spontaneous: arising from an internal cause, resulting from internal or natural processes, with no apparent external influence. A "spontaneously beating cardiomyocyte" is a cell that begins to beat as a result of internal signals.

Stem cell refers to a cell that can generate a fully differentiated functional cell of more than one given cell type. The role of stem cells in vivo is to replace cells that are destroyed during the normal life of an animal. Generally, stem cells can divide without limit. After division, the stem cell may remain as a stem cell, become a precursor cell, or proceed to terminal differentiation. Although appearing morphologically unspecialized, the stem cell may be considered differentiated where the possibilities for further differentiation are limited. A "muscle stem cell" is a stem cell derived from muscle or that gives rise to muscle cells after differentiation. One specific, non-limiting example of a muscle stem cell is a cell that gives rise to cardiac muscle cells.

Subject refers to any mammal, such as humans, non-human primates, pigs, sheep, cows, rodents and the like which is to be the recipient of the particular treatment. In one embodiment, a subject is a human subject or a murine subject.

Suspension: a dispersion of solid particles, such as a cell, throughout the body of a liquid, such as a culture medium or an isotonic (physiologically compatible) buffer.

Therapeutic agent: Used in a generic sense, it includes treating agents, prophylactic agents, and replacement agents.

Therapeutically effective amount is the amount of agent that is sufficient to prevent, treat, reduce and/or ameliorate the symptoms and/or underlying causes of any of a disorder or disease. In one embodiment, a "therapeutically effective amount" is sufficient to reduce or eliminate a symptom of a cardiac disease. In another embodiment, a therapeutically effective amount is an amount sufficient to overcome the disease itself.

A therapeutically effective amount of a cell can be administered in a single dose, or in several doses, for example daily, during a course of treatment. However, the effective amount of the cells will be dependent on the subject being treated, the severity and type of the condition, and the manner of administration of the compound. "Administering" can be accomplished by introducing the therapeutically effective amount locally or systemically into the subject. Systemic introduction can be accomplished by using an intravenous, intramuscular, transcutaneous or subcutaneous means. Such means could include introducing the therapeutically effective amount via injection, or via catheter.

The general term "administering a therapeutically effective amount to the subject" is understood to include all animals (e.g. humans, apes, dogs, cats, horses, and cows) that have or may develop some form of cardiac dysfunction.

Transfected: A transfected cell is a cell into which has been introduced a nucleic acid molecule by molecular biology techniques. As used herein, the term transduction encompasses all techniques by which a nucleic acid molecule might be introduced into such a cell, including transduction with viral vectors, transformation with plasmid vectors, and introduction of DNA by electroporation, lipofection, and particle gun acceleration.

Transplantation: The transfer of a tissue or an organ, or a portion thereof, from one body or part of the body to another body or part of the body.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Unless otherwise defined, all technical and scientific terms used herein have the same meaning as commonly understood by one of ordinary skill in the art. Although methods and materials similar or equivalent to those described herein can be used, suitable methods and materials are described below. In case of conflict, the present specification, including the explanation of terms, will control. In addition, the materials, methods, and examples are illustrative only and not intended to be limiting.

Spoc Cells

Stem cells derived from skeletal muscle (spoc cells) are disclosed herein. Spoc cells do not express the cell surface markers c-met, or c-kit, and are thus termed a c-met–/c-kit– cell. Spoc cells can be isolated from any age mammal, either human or non-human. Thus spoc cells can be obtained from a fetus, a child or an adult of any mammalian species. In one embodiment, a spoc cell is human or murine c-met–/c-kit– cell that can be differentiated into a cardiomyocyte in vitro. In one embodiment, the spoc cell is between about 3 µm and 10 µm in diameter, or are about 4 µm in diameter.

Culture conditions for spoc cells have been identified and are disclosed herein. In one embodiment, spoc cells do not adhere to the culture dish but remain in suspension when cultured in the presence of at least one growth factor. In one specific, non-limiting example, the growth factor is EGF. In another specific, non-limiting example, the growth factor is FGF.

Culture conditions are also disclosed herein (see below) for differentiating spoc cells. The differentiation of spoc cells into cardiomyocytes can be assessed by observing morphological changes. In some examples, differentiated spoc cells are spontaneously beating cardiomyocytes. In several embodiments, organized gap junctions and sarcomeres with clear Z-lines and A- and I-bands, are observed in the differentiated spoc cells. In addition, certain examples of the differentiated spoc cells may be mono- or multi-nucleate. In one embodiment the cells are bi-nucleate.

The isolated spoc cell can be transduced using standard procedures known in molecular biology in order to introduce a nucleic acid molecule of interest into the cell. In one embodiment, the nucleic acid molecule encodes a polypeptide. The polypeptide encoded by the nucleic acid molecule can be from the same species as the cells (homologous), or can be from a different species (heterologous). For example, a nucleic acid molecule can be utilized that supplements or replaces deficient production of a peptide by the tissue of the host wherein such deficiency is a cause of the symptoms of a particular disorder. In this case, the cells act as a source of the peptide. In one specific, non-limiting example the polypeptide is the cardiac specific transcription factor GATA-4.

In one embodiment, the nucleic acid molecule of interest encodes a polypeptide involved in growth regulation or neoplastic transformation of cardiac cells. Specific, non-limiting examples of nucleic acids sequences of interest are SV40 Tag, p53, myc, src, and bcl-2. In another embodiment, the nucleic acid sequence of interest encodes an enzyme. Specific, non-limiting examples of enzymes are proteins involved in the conversion of a pro-drug to a drug, or growth factors that promote the expansion, differentiation, or survival of cardiac progenitor cells, such as EGF, FGF, or atrial natriuretic factor. In yet another embodiment, the nucleic acid sequence of interest encodes a transcriptional regulator.

In one embodiment, the nucleic acid sequence of interest is operably linked to a regulatory element, such as a transcriptional and/or translational regulatory element. Regulatory elements include elements such as a promoter, an initiation codon, a stop codon, mRNA stability regulatory elements, and a polyadenylation signal. A promoter can be a constitutive promoter or an inducible promoter. Specific non-limiting examples of promoters include the CMV promoter, an atrial natriuretic factor promoter, and promoters including TET-responsive element for inducible expression of transgene. In another embodiment, the nucleic acid sequence of interest is inserted into a vector, such as an expression vector. Procedures for preparing expression vectors are known to those of skill in the art and can be found in Sambrook et al., *Molecular Cloning: A Laboratory Manual*, 2nd Ed., Cold Spring Harbor Press, Cold Spring Harbor, N.Y. (1989). Expression of the nucleic acid of interest occurs when the expression vector is introduced into an appropriate host cell.

In yet another specific, non-limiting example, a nucleic acid sequence can be introduced to decrease rejection. For example, the immunogenicity of a cell may be suppressed by deleting genes that produce proteins that are recognized as "foreign" by the host (a knock-out), or by introducing genes which produce proteins, such as proteins that are native to the host and recognized as "self" proteins by the host immune system.

Thus in one embodiment, a spoc cell may be transfected with a nucleic acid molecule designed to functionally delete or "knock-out" a gene of interest. In this method, the nucleic acid molecule of interest is a nucleic acid molecule that undergoes homologous recombination and is inserted into the genome of the spoc cell. Methods for producing "knockouts" in ES cells are known to one of skill in the art (e.g. see U.S. Pat. No. 5,939,598).

According to this example, cells are cultured in vitro as described herein and an exogenous nucleic acid is introduced into the cells by any method known to one of skill in the art, for example, by transfection or electroporation. The transfected cultured cells can then be studied in vitro or can be administered to a subject (see below). Methods for the introduction of nucleic acid sequences into stem cells are known in the art (e.g., see U.S. Pat. No. 6,110,743).

Methods of Isolating and Expanding Muscle Stem Cells

A method of isolating a c-met-/c-kit- cardiomyocyte precursor cell of muscular origin (spoc cell) is described herein. In this method, spoc cells are separated by size from a suspension of muscle cells and the cells are cultured on a solid substrate. The cells that remain in suspension in the culture medium are isolated.

The method of isolation of the spoc cells includes obtaining the cells from the muscle of a subject. Muscle tissue can be prepared for the purpose of isolating or obtaining individual spoc cells by using methods well known to one of skill in the art. Examples of methods of tissue preparation include enzymatic digestion with enzymes such as collagenase, mechanical disruption using instruments such as hand-held or motor-driven homogenizers, or by chemical disruption using, for example, chelators of calcium and magnesium.

The preparation of muscle cells can be sorted by any method that separates cells on the basis of cell size. In one embodiment, the spoc cells are isolated by passing digested skeletal muscle through a series of filters of varying pore size. The cells are passed through two filters, where a first filter has a pore size of about 50–200 μm, about 60–150 μm, about 80–100 μm, or about 100 μm and a second filter has a pore size of about 10–50 μm, 20–40 μm, or about 40 μm. In one embodiment the isolated cells are less than 40 μm in diameter. In other embodiments, isolated cells are between about 3 μm and 10 μm in diameter. In another embodiment the isolated cells are about 4 μm in diameter.

The cells can be also sorted by size by passing them through size-exclusion columns. In one such embodiment, the cells are eluted along a size gradient such that the largest cells are eluted first and the smallest cells are eluted last. The cells can also be sorted by size using FACS. Cells of about 3 μm to 10 μm in diameter, or of about 4 μm in diameter, are isolated.

Once the muscle cells are sorted by size the cells are further selected and then expanded in culture medium. In one embodiment the cells are cultured on a solid substrate that permits the adhesion of a subpopulation of cells in the presence of a culture medium. In one embodiment, the solid substrate is a container, such as a tissue culture dish. In another embodiment, the solid substrate is in the form of beads designed for tissue culture. The medium can be a growth medium, or any buffer that maintains the viability of the cells. A variety of culture media are known and are suitable for use. Generally, the growth medium includes a minimal essential medium. In one embodiment, the medium is DMEM and/or F12, or a combination of DMEM and F12 (at a ratio between about 1:1 to about 10:1).

The growth medium may be supplemented with serum. Specific, non-limiting examples of serum are horse, calf or fetal bovine serum. The medium can have between about 3% by volume to about 10% by volume serum, or about 5% by volume serum.

In one embodiment, the medium contains one or more additional additives such as nutrients. Specific, non-limiting examples of these nutrients are shown in the table below:

| Additive | Exemplary Concentration |
| --- | --- |
| serum | About 3% to about 10% |
| insulin | About 5 μg/ml to about 10 μg/ml |
| transferrin | About 5 μg/ml to about 10 μg/ml |
| selenium | About 6 ng/ml |
| ethanolamine | About 2 μg/ml |
| EGF | About 5 ng/ml to about 10 ng/ml |
| FGF | About 5 ng/ml to about 10 ng/ml |
| gentamycin | About 25 μg/ml to about 50 μg/ml |
| fungizone | About 0.2 μg/ml to about 2.5 μg/ml |

The muscle stem cell growth media can also be supplemented with growth factors. In one embodiment, the growth medium includes basic fibroblast growth factor (bFGF). In one specific example, the growth medium includes between about 2 ng/ml to about 100 ng/ml of bFGF, such as for example between about 5 ng/ml to about 50 ng/ml, between about 8 ng/ml to about 20 ng/ml, or between about 5 to about 10 ng/ml bFGF. In yet another example, the medium includes about 10 ng/ml bFGF. In another embodiment, the growth medium includes epidermal growth factor (EGF). In one specific example, the growth medium includes between about 2 ng/ml to about 100 ng/ml of EGF, such as for example between about 5 ng/ml to about 50 ng/ml, between about 8 ng/ml to about 20 ng/ml, or between about 5 ng/ml to about 10 ng/ml EGF. In yet another example, the medium includes about 10 ng/ml EGF. Thus in one embodiment, the growth medium is 1:1 DMEM/F12 and includes 5% fetal bovine serum, 10 ng/ml FGF, 10 ng/ml EGF, 5 μg/ml insulin, 5 μg/ml transferrin, 6 ng/ml selenium, 2 μg/ml ethanolamine.

In one specific, non-limiting example the cells are cultured in the growth medium for about 4 days to about 8 days. In another specific, non-limiting example, the cells are cultured in the growth medium for about 6 days to about 7 days.

During the period that the cells are cultured in the presence of growth factors, the cells cluster and increase in size. Within the clusters the cells are between about 5–20 μm in diameter, or between about 10–14 μm in diameter.

A method is also provided for isolating spoc cells wherein the spoc cells are identified using specific binding agents, such as antibodies, for example monoclonal antibodies that recognize cell surface markers. This particular method of isolation of the spoc cells includes obtaining the cells from the muscle of a subject, as described above. In one embodiment, the cells are selected by size (see above) and then the c-met-/c-kit- spoc cells are identified using the specific binding agents, such as antibodies that recognize the c-met and c-kit cell surface markers.

In one embodiment the c-met and c-kit antibodies are immobilized. A particular embodiment uses magnetic cell sorting. This method involves a combination of monoclonal antibodies which are covalently bound to the surface of magnetic beads and which are directed to cell surface markers which are absent from the cells being selected. For example, to isolate the c-met-/c-kit- spoc cells, monoclonal antibodies to c-met and c-kit bound to magnetic beads are used. All cells expressing either c-met, or c-kit, or both c-met and c-kit, will be bound by the antibodies and retained by the beads. Since the cells bound to the magnetic beads are immobilized by the magnet, the c-met–/c-kit– cells that remain in suspension can be isolated from the other cells.

In another embodiment, purified populations of c-met–/c-kit– spoc cells are isolated via FACS. Fluorescent-tagged antibodies against c-met and c-kit identify c-met+, c-kit+ and c-met+/c-kit+ double-positive populations of cells, allowing for the identification and isolation of the double-negative c-met–/c-kit– population.

In other embodiments a single antibody, or a combination of antibodies, can be covalently bound to inert beads, such as sepharose beads. The beads can be packed in a column or maintained as a slurry. The cells expressing one or more of the cell surface markers are recognized by one or more of the antibodies, thus becoming bound to the beads, thereby identifying a subpopulation of unbound cells that does not express the combination of cell surface markers.

In another embodiment the antibodies are not immobilized. In a particular embodiment the addition of the antibodies to a mixture of cells causes the aggregation of cells expressing the cell surface markers recognized by the antibodies. The cells not expressing the cell surface markers are excluded from the aggregates and can be isolated.

Spoc cells isolated by these or other methods can be maintained in culture. The spoc cells can further be differentiated into cardiomyocytes.

Methods of Differentiating Muscle Stem Cells

A method is disclosed herein for differentiating a spoc cell into a cardiomyocyte. In a particular example, the cardiomyocyte is a spontaneously beating cardiomyocyte.

In one embodiment, differentiation into cardiomyocytes is induced by culturing cells in medium similar to the growth medium, but which does not include at least one growth factor. Thus, a specific, non-limiting example of a differentiation medium is a growth medium that lacks at least one growth factor. Growth factors removed from the medium include, but are not limited to, bFGF or EGF, or a combination of bFGF and EGF.

Removal of at least one growth factor causes the cells to adhere to the tissue culture dish and acquire characteristics of a differentiated cardiomyocyte. Differentiation refers to the process whereby relatively unspecialized cells, such as the c-met–/c-kit– muscle-derived stem cells acquire specialized structural and/or functional features characteristic of mature cells, such as cardiomyocytes.

Differentiation of c-met–/c-kit– muscle stem cells into cardiomyocytes, such as spontaneously beating cardiomyocytes, can be measured by any method known to one of skill in the art. Specific, non-limiting examples are immunohistochemical analysis to detect expression of cardiac polypeptides (e.g. troponin-T, L-type calcium channel, or cardiac-specific transcription factors GATA-4, or Nkx2.5), or assays such as ELISA assay and Western blot analysis. Differentiation of cells can also be measured by assaying the level of mRNA coding for cardiac polypeptides using techniques such as Northern blot, RNase protection and RT-PCR. In another embodiment, the number of spontaneously beating cells is assessed.

Calcium transients, or the flux in intracellular calcium concentrations, can be used as a measure of cardiomyocyte differentiation. In one embodiment calcium imaging is used to measure calcium transients. For example, ratiometric dyes, such as fura-2, fluo-3, or fluo-4 are used to measure intracelluar calcium concentration. The relative calcium levels in a population of cells treated with a ratiometric dye can be visualized using a fluorescent microscope or a confocal microscope. In other embodiments, the membrane potential across the cell membrane is monitored to assess calcium transients. For example, a voltage clamp is used. In this method, an intracellular microelectrode is inserted into the cardiomyocyte.

In one embodiment, calcium transients can be seen before observable contractions of the cardiomyocytes. In other embodiments calcium transients are seen either during, or after, observable contractions of cardiomyocytes. In another embodiment the cells are cultured in the presence of conditions wherein the cells do not beat, such as in the presence of a calcium chelator (e.g. EDTA or EGTA) and the calcium transients are measured.

Methods for Treatment of Cardiac Diseases or Disorders

In other embodiments, methods are provided for treating a subject suffering from a disease or a disorder, such as myocardial injury, or alleviating the symptoms of such a disorder, by administering cells isolated and cultured according to the methods disclosed.

In one embodiment, spoc cells are isolated as described herein and a therapeutically effective amount of spoc cells is administered to the subject. In another embodiment, spoc cells are isolated and differentiated into cardiomyocytes, as disclosed above, and a therapeutically effective amount of the differentiated cells are administered to a subject, such as a human. The cells may be administered in any fashion, for example in a dose of, for example $0.25-1.0 \times 10^6$ cells. Different dosages can of course be used depending on the clinical circumstances. The cells may be administered systemically (for example intravenously) or locally (for example directly into a myocardial defect under echocardiogram guidance, or by direct application under visualization during surgery). In another example, the cells are administered in a gel matrix (such as Gelfoam from Upjohn Company) which polymerizes to form a substrate in which the administered cells can grow.

In one embodiment the subject has a myocardial injury. The myocardial injury may be due to trauma that occurred as the result of an object or projectile, such as a knife or a bullet, having penetrated the myocardium, or as a consequence of surgery to remove, for example, a tumor. Myocardial injury may also result from diseases such as cardiomyopathy, myocardial infarction, or congenital heart disease. In another embodiment the subject is suffering from cardiac dysfunction which includes, for example, abnormal or improper functioning of the heart valves, or abnormal communication between the chambers of the heart.

In one embodiment the spoc cells or differentiated cardiomyocytes are administered systemically by injection. Specific, non-limiting examples include administration by subcutaneous injection, intramuscular injection, or intravenous injection. If administration is intravenous, an injectible liquid suspension of spoc cells can be prepared and administered by a continuous drip or as a bolus.

In another embodiment, the spoc cells or differentiated cardiomyocytes are administered locally. One specific, non-limiting example of local administration is intra-cardiac muscle injection. For intra-cardiac injection, the spoc cells are in an injectible liquid suspension preparation or in a biocompatible medium which is injectible in liquid form and becomes semi-solid at the site of damaged myocardium. A conventional intra-cardiac syringe or a controllable endoscopic delivery device can be used so long as the needle lumen or bore is of sufficient diameter (e.g. 30 gauge or larger) that shear forces will not damage the spoc cells.

In other embodiments the cells are administered locally on a support medium. One specific, non-limiting example of a support medium is a sterile mesh, or matrix, upon which the cardiomyocytes are cultured. A layer of cardiomyocytes, for example a confluent layer of cardiomyocytes, cultured on such a matrix can be applied locally, or grafted at or near, a site of myocardial injury. In one embodiment the support medium is a biodegradable mesh. In another embodiment the support medium is not biodegradable. The size of the mesh, and the density of cells on it, can vary depending on the myocardial defect being treated.

In another embodiment the cells are encapsulated prior to administration., such as by co-incubation with a biocompatible matrix known in the art. A variety of encapsulation technologies have been developed (e.g. Lacy et al., *Science* 254:1782–84, 1991; Sullivan et al., *Science* 252:7180712, 1991; WO 91/10470; WO 91/10425; U.S. Pat. No. 5,837, 234; U.S. Pat. No. 5,011,472; U.S. Pat. No. 4,892,538). During open surgical procedures, involving direct physical access to the heart, all of the described forms of spoc cell delivery preparations are available options.

The cells can be repeatedly administered at intervals until a desired therapeutic effect is achieved.

Use of Spoc Cells Produced to Screen Agents that Affect Cardiomyocyte Differentiation or Function In other embodiments, methods are provided for screening agents that affect cardiomyocyte differentiation or function. According to this method, a population of cardiomyocytes or their precursors is produced as described above. The population of cells is contacted with an agent of interest, and the effect of the agent on the cell population is then assayed. The effect on differentiation, survival, proliferation, or function of the cells is assessed.

The methods described herein can be used to assess the effect of an agent on cardiomyocyte differentiation. In order to assess the effect of a test agent on cardiomyocyte differentiation or function, the agent is contacted either to spoc cells or CS cells. In several embodiments the spoc cells are maintained in medium including a growth factor between about 1 day to about 8 days, between about 4 days to about 7 days, or about 7 days before the addition of an agent.

In another embodiment the growth factor is removed from the medium, generating CS cells, at or before the agent is added. In several specific, non-limiting examples CS cells are maintained in the medium between about 1 day to about 56 days, between about 7 days to about 28 days, or between about 14 days to about 21 days before the addition of an agent.

Differentiation of spoc cells contacted with an agent can be assessed by any means known to one of skill in the art. In one embodiment the morphology is examined, for example electron microscopy is used to assess the ultrastructure of the cells. Suitable parameters for evaluation include, but are not limited to the evaluation of gap junctions between contacting cardiomyocytes. In other embodiments, immunohistochemical or immunofluorescence techniques are used to assess differentiation. In yet another embodiment, differentiation is assessed by analysis expression of specific mRNA molecules expressed in cardiomyocytes. Suitable assay systems include, but are not limited to RT-PCR, in situ hybridization, Northern analysis, or RNase protection assays. In a further embodiment the levels of polypeptides expressed in differentiated cardiomyocytes are assayed. Specific, non-limiting examples of polypeptide assays of use include Western blot analysis, ELISA assay, or immunofluorescence. Alternatively, calcium transients are measured, as described above. The assay can also be used to screen the effect of an agent on cardiomyocyte function. Any method known to one of skill in the art can be utilized to assess cardiac function. In one embodiment the beating rate of a cardiomyocyte is assayed to identify agents that increase or decrease beating. One method for assessing the beating rate is to observe beating under a microscope. Agents that can be screened in this manner include inotropic drugs, such as sympathomimetic agents.

In one embodiment, cells contacted with the agent are compared with a control. Suitable controls include spoc or CS cells not contacted with the agent, or contacted with vehicle alone. Standard values can also be used as a control.

Kits

The cells described herein are ideally suited for the preparation of a kit. The kit can include a carrier means, such as a box, a bag, or plastic carton. In one embodiment the carrier contains one or more containers such as vials, tubes, and the like that include a sample of spoc cells. In another embodiment, the carrier includes a container with an agent that affects differentiation, a buffer, or a vehicle for the introduction of the cells. Instructions can be provided to detail the use of the components of the kit, such as written instructions, video presentations, or instructions in a format that can be opened on a computer (e.g. a diskette or CD-ROM disk). These instructions indicate, for example, how to administer the cells to treat a myocardial defect or how to use the cells to screen test agents of interest (such as inotropic drugs).

Without further elaboration, it is believed that one skilled in the art can, using this description, utilize the present invention to its fullest extent. The following examples are illustrative only, and not limiting of the remainder of the disclosure in any way whatsoever.

EXAMPLES

Example 1

Method of Isolating and Expanding Cardiomyocyte Precursor Cells From Adult Mouse Skeletal Muscle Skeletal muscle tissue from hind legs of 6–10 week-old male C57B1/SJ6 mice was cut into small pieces and digested with collagenase for two hours at 37° C. The digested tissue was cleared of cell debris and other undigested tissue fragments by passage through a 100 μm filter and then through a 40 μm filter (Falcon). The cell suspension was centrifuged at low speed (1,400 rpm) to clear as much as of the small muscle fiber fragments as possible. The cells at this stage consisted mostly of clusters of small round cells approximately 4 μm in diameter, called spoc (skeletal-based precursors of cardiomyocytes) cells.

The spoc cells were plated at a density of approximately $10^5$ cells per $cm^2$ in regular tissue culture dishes in complete growth medium (1:1 DMEM/F12 supplemented with 5% fetal bovine serum (FBS), 10 ng/ml human EGF, 10 ng/ml human bFGF (PeproTech, Inc.), 5 μg/ml insulin, 5 μg/ml transferrin, 6 ng/ml selenium, 2 μg/ml ethanolamine (ITS-X, Invitrogen Corporation), 25 μg/ml gentamicin and 2.5 μg/ml fungizone (Life Technologies)). After a few days, the culture consisted of a floating population of round cells and some adherent fibroblasts. The round cells enlarged as they underwent a few rounds of cell division during which time they became clusters of floating round cells with an increased diameter of 10–14 µm. The cells in these clusters, were referred to as CS (cardiac precursors from spoc) cells.

Example 2

Method of Differentiating Spoc Cells Into Cardiomyocytes

CS cells were gently collected after seven days of growth in complete growth medium. The cells were then plated in the same medium in the absence of EGF and bFGF (differentiation medium) and were maintained at 37° C. To assess the progression of differentiation of the cells, the cultures were observed at various time points using an inverted light microscope. Beating frequency measurements of the cardiomyocytes were obtained by video microscopy.

Under the differentiation culture conditions the cells gradually began to attach to the culture dish, and elongate in shape, taking on the appearance of myoblasts. Within a few days of being maintained in the differentiation medium, the cells began spontaneously beating. Elongated uninucleate cells (60 µm in length) and round uninucleate cells (15 µm in diameter) both exhibited spontaneous beating. By four days post replating the beating cells were more numerous. The beating cells did not undergo any more cell divisions and were maintained in this medium for several weeks, with the maintenance of the spontaneous beating phenotype. Spontaneous beating was continuous and measured at a frequency of 1–8 Hz. Small contractions observed in a day 14 cell (30 µm in length) were likely the consequence of an immature contractile apparatus (FIG. 1C). Cells kept at room temperature beat continuously for at least 3 hours.

Example 3

Detection of Cardiac-Specific Polypeptides by Immunofluorescence

The specimens were air-dried for 30 minutes and then fixed in 4% paraformaldehyde at 4° C. followed by a rinse for 5 minutes with phosphate buffered saline (PBS). They were blocked with goat serum for 30 minutes and then incubated overnight, at 4° C., with either GATA-4 (mAb H-112, Santa Cruz Biotechnology), sarcomeric myosin (MF-20 Ab, ATTC), cardiac-specific troponin-T (mAb RDI-TRK4T19–1A11, Molecular Probes, Inc.), cardiac L-type calcium channel (mAB AB5412–2000U1a, Chemicon Inc.), cardiac-specific transcription factor Nkx2.5 (mAb N-19, Santa Cruz Biotechnology), or connexin 43 (mAb 71-07000, Zymed Laboratories Inc.) (1:200). Following the overnight incubation, the specimens were rinsed 3 times (5 minutes each) with PBS and blocked again with goat serum for 30 minutes. The specimens were then incubated at room temperature with a secondary antibody, conjugated with either Fluorescein Isothiocyanate (FITC), Texas Red, or Tetramethylrhodamine Isothiocyanate (TRITC), for 1 hour. They were again rinsed 3 times (5 minutes each) with PBS and then visualized with a laser confocal microscope (Leica) to detect fluorescent signals.

The earliest time of GATA-4 expression is after 3 days in culture in growth factor containing medium. Within 3 days after replating the cells in differentiation medium, some cells begin to express sarcomeric myosin. Cytospins of day 7 CS cells stained with monoclonal antibodies demonstrate the expression of cardiac-specific transcription factor GATA-4, sarcomeric myosin, and cardiac-specific troponin-T. Day 14 cells stained for GATA-4 and sarcomeric myosin. Overlays of images of cells stained with GATA-4 and sarcomeric myosin demonstrated that they were co-localized in the cell. At this early stage in development some cells may either be positive for GATA-4 or sarcomeric myosin. By day 28, the majority of cells express both proteins. By day 21 the cells are positive for cardiac L-type calcium channel, cardiac-specific transcription factor Nkx2.5, and connexin 43.

Example 4

Ultrastructure of Differentiated Cardiomyocytes

For routine transmission electron microscopy, cells were fixed in situ on Petri dishes with 1.25% glutaraldehyde in 0.1 M cacodylate buffer containing 1% $CaCl_2$ at 4° C. for 2 hours. Following fixation, cells were washed three times in Sabatini's solution (0.1 M cacodylate buffer containing 6.8% sucrose), and post-fixed with 1% osmium tetroxide in cacodylate buffer for one hour. After three washes in Sabatini's solution, samples were dehydrated in alcohol and embedded in Scipoxy 812 (Energy Beam Sciences, Inc. Agawarm, Mass.). Polymerization was carried out at 37° C. for 24 hours and then at 60° C. overnight. Ultra-thin sections were cut with a Leica Ultracut UCT ultramicrotome, stained with uranyl acetate and Reynold's lead citrate, and examined with a JEOL 1200 CXII transmission electron microscope.

In FIG. 1, transmission electron micrographs show the progression of CS cells. At day 3 round cells with disordered myosin filaments (FIG. 1A) and large central nuclei surrounded by copious mitochondria (FIG. 1D, box and detail) exist. By day 7 elongated cells (FIG. 1E) contain dense bodies (FIG. 1E arrowhead and FIG. 1B, lower box). Myosin filaments of characteristic 1.6 µm-length (FIG. 1B, top box) radiate outward. A day 14 cell (FIGS. 1C and F) with a single, central nucleus shows a stretching out of the dense bodies (FIG. 1C) into an organizing sarcomere. By day 56, a well-defined sarcomere (FIG. 1G) is present, with identifiable A- and I-bands and Z-lines.

Example 5

Calcium Transients as a Measure of Cardiomyocyte Differentiation

Cardiomyocytes were incubated for 30 minutes at 37° C. with fluo-3 or fluo-4 dye at a concentration of approximately 5–10 µm in DMEM/F-12 (dyes dissolved in DMSO 1:1 with pluronic solution). The cells were then washed with fresh DMEM/F-12. The images were collected with a Zeiss LSM-510 laser scanning confocal system and a C-Apochromat 63× objective (1.2 N.A.). Fluo-3 and fluo-4 were excited at 488 nm with an argon laser and the emission light was collected using an LP 505 filter. The pinhole was adjusted to produce a 5 µm slice to minimize the influence of axial movements with contraction on viewing the calcium transients. All transmitted light images were collected simultaneously using a transmitted light detector in conjunction with the 488 nm excitation light. Data depth for the images was 8-bit.

Figure 2:
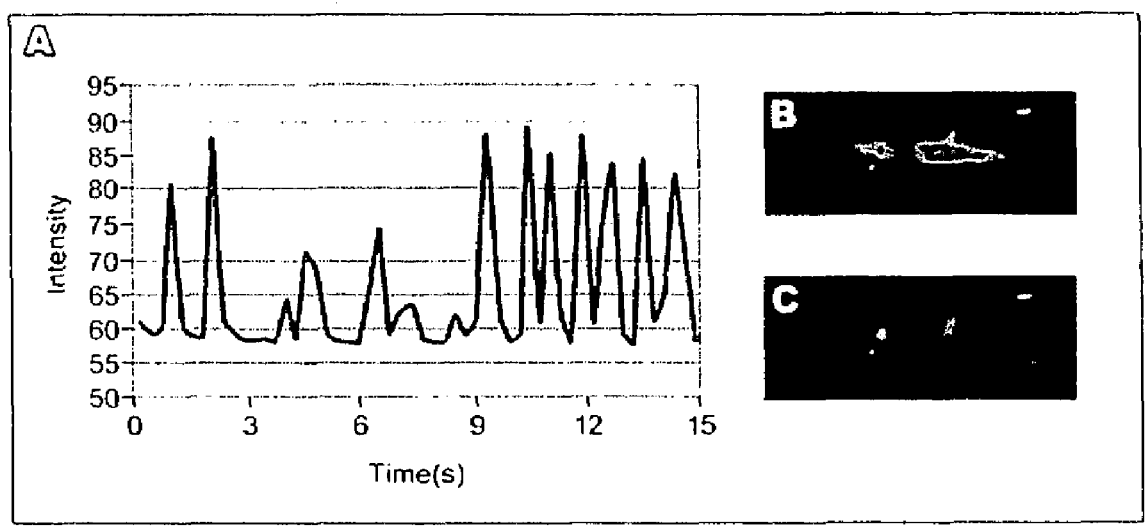
FIG. 2 demonstrates the existence of calcium transients, in cardiomyocytes differentiated from CS cells.

Calcium transients can be observed with confocal microscopy in fluo-3- and fluo-4-treated cells (FIG. 2). Fluorescent intensity is proportional to the amount of calcium binding to fluo-3 dye upon release of calcium from the sarcoplasmic reticulum. FIG. 2A shows a graphical representation of the calcium transient in a beating CS cell-derived cardiomyocyte. Peak intensity and baseline are shown in FIG. 2B and FIG. 2C, respectively. In some CS cells, calcium transients can be seen before observable contractions are noted, suggesting the development of cardiomyocyte excitation elements in advance of maturing contractile elements.

Example 6

Distinguishing Spoc Cells From Bone Marrow Cells

Spoc cells are c-kit−, distinguishing them from the c-kit+ bone marrow cells that have been used directly or indirectly in experiments to reconstitute infarcted heart. Despite this, spoc cells could be derived from circulating bone marrow cells that become c-kit⁻ after migration to skeletal muscle. In order to more fully evaluate this question, whole bone marrow was fractionated into c-kit+ and c-kit− populations. Both separate and combined populations were cultured under the same conditions as spoc cells. None of the 3 marrow cell populations developed into spontaneously beating cells.

To test whether marrow cells have the potential to differentiate into cardiomyocytes in the presence of soluble factors released from spoc cells, equal proportions of marrow and spoc cells were co-cultured in a Costar transwell system, in which the two chambers are separated by a 0.4 μm permeable membrane. Although the total number of cells increased in each compartment, the spoc cells alone differentiated into beating cells expressing cardiac markers.

In order to test if cell-cell contact between bone marrow and spoc cells would lead bone marrow cells to differentiate into cardiomyocytes, total bone marrow was mixed in equal proportion with EGFP-expressing spoc cells obtained from EGFP-expressing transgenic mice (ACTbEGFP, The Jackson Laboratory). In three separate experiments, under the same culture conditions, total cell number increased, but only EGFP-expressing cells developed into beating cells. The converse experiments showed a similar increase in cell number, but beating cells did not express EGFP. Taken together, these experiments show that bone marrow does not contain any cell population phenotypically similar to spoc cells isolated from skeletal muscle.

Example 7

Distinguishing Spoc Cells From Cells Derived From the Heart

In order to determine if spoc cells can be isolated from heart, as well as skeletal muscle, the two tissues from the same mouse were dissociated and cultured separately. Only the spoc cell preparation from skeletal muscle differentiated into beating cells expressing cardiac markers. Two replicate co-culture experiments of both cell populations in Costar transwell systems produced an increased number of cells in both chambers, but again, only the skeletal muscle-derived cells developed into beating cells expressing cardiac markers.

Example 8

Distinguishing Spoc Cells From Mesenchymal Stem Cells

To determine if spoc cells can be distinguished from mesenchymal stem cells (MSC), MSC were compared to spoc cells in culture. The MSC (Clonetics Corporation) were cultured in parallel with spoc cells generated from skeletal muscle as described in the methods above. The MSC adhered to the plate almost immediately upon plating, remained adherent throughout 12 days of observation, and did not show any sign of beating. In contrast, the cardiac progenitor cells from skeletal muscle were smaller in size, remained nonadherent while they developed into floating clusters of spoc cells, and they progressed to beating cardiac myocytes expressing cardiac markers. Spoc cells did not form in the MSC cultures. Thus, spoc cells are not MSC.

Example 9

In Vivo Differentiation of Spoc Cells

In order to determine if spoc cells are capable in vivo of continuing along the same differentiation pathway observed in vitro, approximately 100,000 EGFP-expressing, GATA-4-negative spoc cells were injected via tail vein into a mouse two months after an induced myocardial infarction (created by left coronary artery ligation). Two weeks later, histologic examination of the heart showed EGFP positive cells that were now also GATA-4 positive, located in the peripheral region of the infarct. Since spoc cells are not GATA-4 positive, these findings indicate that these cells can home to an area of cardiac damage and begin to differentiate into cardiomyocytes, as they do in vitro.

Example 10

Distinguishing Spoc Cells From Satellite Cells

Spoc cells and satellite cells are air-dried on glass slides for 30 minutes and then fixed in 4% paraformaldehyde at 4° C. followed by a rinse for 5 minutes with PBS. The cells are blocked with goat serum for 30 minutes and then incubated overnight, at 4° C., with rabbit anti-met (1:200, Santa Cruz Biotechnology). Following the overnight incubation, the slides are rinsed 3 times (5 minutes each) with PBS and blocked again with goat serum for 30 minutes. The cells are then incubated at room temperature with a secondary antibody, conjugated with Fluorescein Isothiocyanate (FITC) for 1 hour. They are again rinsed 3 times (5 minutes each) with PBS and then visualized with a laser confocal microscope (Leica) to detect fluorescent signals. Of the two cell types examined, only the satellite cells are positively stained with c-met indicating that satellite cells express c-met on their cell surface, whereas spoc cells do not.

Example 11

Method of Isolating Cardiomyocyte Precursor Cells From Adult Human Skeletal Muscle Skeletal muscle tissue is surgically obtained from the deltoid muscle of an adult human, is cut into small pieces and is digested with collagenase for two hours at 37° C. The digested tissue is cleared of cell debris and other undigested tissue fragments by passage through a 100 μm filter and then through a 40 μm filter. The cell suspension is centrifuged at low speed to clear as much of the small muscle fiber fragments as possible. The cells at this stage consist mostly of clusters of small round cells approximately 4 μm in diameter which are the human spoc cells. These cells do not express the satellite cell surface marker c-met.

The spoc cells are plated at a density of approximately $10^5$ cells per cm$^2$ in regular tissue culture dishes in complete growth medium (1:1 DMEM/F12 supplemented with 5% fetal bovine serum (FBS), 10 ng/ml human EGF, 10 ng/ml human bFGF (PeproTech, Inc.), 5 µg/ml insulin, 5 µg/ml transferrin, 6 ng/ml selenium, 2 µg/ml ethanolamine (ITS-X, Invitrogen Corporation), 25 µg/ml gentamicin and 2.5 µg/ml fungizone (Life Technologies)). After a few days, the culture consists of a floating population of round cells and some adherent fibroblasts. The round cells enlarge as they undergo a few rounds of cell division during which time they become clusters of floating round cells with an increased diameter of 10–14 µm. The cells in these clusters were referred to as CS (cardiac precursors from spoc) cells.

In view of the many possible embodiments to which the principles of our invention may be applied, it should be recognized that the illustrated embodiments are only examples of the invention and should not be taken as a limitation on the scope of the invention. Rather, the scope of the invention is defined by the following claims. We therefore claim as our invention all that comes within the scope and spirit of these claims.

We claim:

1. An isolated population of mouse c-kit-/c-met- cardiomyocyte precursor cells obtained from adult mouse skeletal muscle, wherein the mouse cardiomyocyte precursor cells are between about 3 µm and 10 µm in diameter.

2. The cells of claim 1, wherein the cells are in suspension.

3. The cells of claim 1, wherein the cells are approximately 4 µm in diameter.

4. The cells of claim 1, wherein the cells differentiate into cardiomyocytes, wherein the cardiomyocytes express a combination of polypeptides selected from the group consisting of GATA-4, troponin-T, L-type calcium channel, and Nkx2.5.

5. The cells of claim 1, wherein the cells differentiate into spontaneously beating cardiomyocytes.

6. The cells of claim 1, wherein the cells are transduced with a viral vector.

7. The cells of claim 6, wherein the viral vector comprises a heterologous nucleic acid.

8. A mouse c-kit-/c-met- cardiomyocyte precursor cell obtained from adult mouse skeletal muscle isolated by a method comprising:

separating adult mouse skeletal muscle cells of less that 40 µm in diameter from a suspension of cells;

culturing the adult mouse skeletal muscle cells in a tissue culture medium on a solid substrate; and isolating the mouse c-kit-/c-met- cardiomyocyte precursor cells, wherein the mouse c-kit-/c-met- cardiomyocyte precursor cells are between about 3 µm and 10 µm in diameter and are in suspension in the tissue culture medium.

9. A pharmaceutical composition comprising the mouse c-kit-/c-met- cardiomyocyte precursor cells of claim 1 in a pharmaceutically acceptable carrier.

10. A kit for promoting cardiomyocyte differentiation, comprising a container containing a purified population of mouse c-kit-/c-met- cardiomyocyte precursor cells obtained from adult mouse skeletal muscle, wherein the mouse cardiomyocyte precursor cell is between about 3 µm and 10 µm in diameter.

11. The kit of claim 10, further comprising a container containing a growth factor, a container containing a culture medium, instructions for using the kit, or any combination thereof.

12. An isolated mouse c-kit-/c-met- cardiomyocyte precursor cell obtained from adult mouse skeletal muscle, wherein the mouse cardiomyocyte precursor cell is between about 3 µm and 10 µm in diameter and differentiates into a spontaneously beating cardiomyocyte.

13. The cell of claim 12, wherein the cell is approximately 4 µm in diameter.

14. The cell of claim 12, wherein the cell is transduced with a viral vector.

15. The cell of claim 14, wherein the viral vector comprises a heterologous nucleic acid.

16. The cell of claim 12, wherein the cardiomyocyte expresses GATA-4, troponin-T, L-type calcium channel, or Nkx2.5, or a combination thereof.

17. A pharmaceutical composition comprising the mouse c-kit-/c-met- cardiomyocyte precursor cell of claim 12 in a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,220,582 B2 | Page 1 of 2 |
| APPLICATION NO. | : 10/863004 | |
| DATED | : May 22, 2007 | |
| INVENTOR(S) | : Epstein et al. | |

It is certified that error appears in the above-identified patent and that said Letters Patent is hereby corrected as shown below:

On the Title Page Item (56) OTHER PUBLICATIONS:

Page 1, right column, "comparison of vectors," should read --comparison of viral vectors,"--.

Column 1, line 64, "Jackson et al," should read --Jackson et al.,--.

Column 2, line 35, "of a several embodiments which proceeds" should read --of several embodiments, which proceeds--.

Column 2, line 49, "nucleus shows" should read --nucleus that shows--.

Column 3, line 28, "1-56081-569-8)" should read --1-56081-569-8).--.

Column 5, line 21, "Medium A" should read --Medium: A--.

Column 5, line 34, "tern" should read --term--.

Column 8, line 10, "Remington'S" should read --Remington's--.

Column 8, line 34, "Polypeptide refers" should read --Polypeptide: Refers--.

Column 10, line 33, "Spontaneous: arising" should read --Spontaneous: Arising--.

Column 10, line 37, "Stem cell refers" should read --Stem cell: Refers--.

Column 10, line 50, "Subject refers" should read --Subject: Refers--.

Column 10, line 55, "Suspension: a" should read --Suspension: A--.

Column 17, line 16, "administration.," should read --administration,--.

Column 17, line 19, "252:7180712" should read --252:718-712--.

UNITED STATES PATENT AND TRADEMARK OFFICE
CERTIFICATE OF CORRECTION

PATENT NO. : 7,220,582 B2
APPLICATION NO. : 10/863004
DATED : May 22, 2007
INVENTOR(S) : Epstein et al.

It is certified that error appears in the above-identified patent and that said Letters Patent is hereby corrected as shown below:

Column 18, lines 55-56, "as much as of" should read --as much of--.

Column 20, lines 25-26, "Inc. Agawarm," should read --Inc., Agawarm,--.

Column 22, line 63, "as much as of" should read --as much of--.

Column 23, line 37, in Claim 5, "differentiates" should read --differentiate--.

Column 24, lines 1-2, in Claim 8, "less that 40μM" should read --less than 40μM--.

Signed and Sealed this

Twenty-ninth Day of September, 2009

David J. Kappos
*Director of the United States Patent and Trademark Office*